(12) United States Patent
Hauel et al.

(10) Patent No.: US 8,993,778 B2
(45) Date of Patent: Mar. 31, 2015

(54) PROCESS FOR MANUFACTURE OF TELMISARTAN

(71) Applicants: Norbert Hauel, Schemmerhofen (DE); Rolf Dach, Gau-Algesheim (DE); Helmut Heitger, Ingelheim am Rhein (DE); Oliver Meyer, Dorsheim (DE)

(72) Inventors: Norbert Hauel, Schemmerhofen (DE); Rolf Dach, Gau-Algesheim (DE); Helmut Heitger, Ingelheim am Rhein (DE); Oliver Meyer, Dorsheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 126 days.

(21) Appl. No.: 13/750,551

(22) Filed: Jan. 25, 2013

(65) Prior Publication Data

US 2013/0137878 A1    May 30, 2013

Related U.S. Application Data

(63) Continuation of application No. 13/084,728, filed on Apr. 12, 2011, now abandoned, which is an application for the reissue of Pat. No. 7,193,089.

(60) Provisional application No. 60/465,952, filed on Apr. 28, 2003.

(30) Foreign Application Priority Data

Mar. 31, 2003  (DE) .................. 103 14 702

(51) Int. Cl.
*C07D 235/04* (2006.01)
*C07D 403/04* (2006.01)
*C07D 235/20* (2006.01)
*C07D 235/18* (2006.01)

(52) U.S. Cl.
CPC ............ *C07D 235/20* (2013.01); *C07D 235/18* (2013.01)

USPC .................. 548/305.4; 548/302.7

(58) Field of Classification Search
CPC .......................... C07D 235/04; C07D 403/04
USPC ............................ 548/301.7, 305.4
See application file for complete search history.

(56) References Cited

U.S. PATENT DOCUMENTS 5,385,925 A * 1/1995 Narr et al. ............... 514/382
5,684,029 A * 11/1997 Narr et al. ............... 514/394
7,193,089 B2 * 3/2007 Hauel et al. ............. 548/305.4

OTHER PUBLICATIONS

Narr et al (1992): STN International HCAPLUS database, Columbus (OH), accession No. 1992: 448554.*

* cited by examiner

*Primary Examiner* — Golam M M Shameem
(74) *Attorney, Agent, or Firm* — Michael P. Morris; Edouard G. Lebel; Usha R. Patel

(57) ABSTRACT

A process for preparing telmisartan by reacting 2-n-propyl-4-methyl-6-(1'-methylbenzimidazol-2'-yl)benzimidazole with a compound of formula (IV)

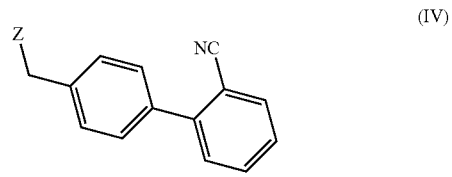

(IV)

wherein Z is a leaving group, to obtain the compound 2-cyano-4'-[2"-n-propyl-4"-methyl-6"-(1'''-methylbenzimidazol-2'''-yl)benzimidazol-1"-ylmethyl]biphenyl, and subsequently hydrolyzing the nitrile function to obtain the acid function.

26 Claims, No Drawings

PROCESS FOR MANUFACTURE OF TELMISARTAN

RELATED APPLICATIONS

This application claims benefit of U.S. Ser. No. 60/465,952, filed Apr. 28, 2003, and claims priority to German Application No. 103 14 702.0, filed Mar. 31, 2003, each of which is hereby incorporated by reference in its entirety.

FIELD OF THE INVENTION

The present invention relates to a new process for preparing 4'-[2-n-propyl-4-methyl-6-(1-methylbenzimidazol-2-yl)benzimidazol-1-ylmethyl]biphenyl-2-carboxylic acid (INN: telmisartan).

BACKGROUND OF THE INVENTION

Telmisartan is an angiotensin II receptor antagonist which is suitable for the treatment of high blood pressure and other medical indications as described in EP 502314 B 1. The active substance has the following structure:

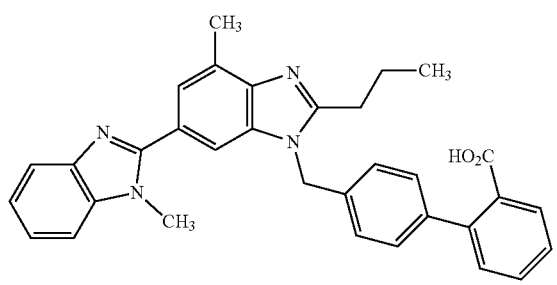

Telmisartan is generally prepared and sold in the form of the free acid. As disclosed in WO 00/43370, crystalline telmisartan occurs in two polymorphic forms which have different melting points. Under the influence of heat and moisture, the lower-melting polymorphic form B changes irreversibly into the higher-melting polymorphic form A.

Hitherto, telmisartan has been synthesized industrially by reacting 2-n-propyl-4-methyl-6-(1'-methylbenzimidazol-2'-yl)benzimidazole (I) with tert-butyl 4'-bromomethylbiphenyl-2-carboxylate (H) and subsequently saponifying according to the following Diagram 1.

Diagram 1

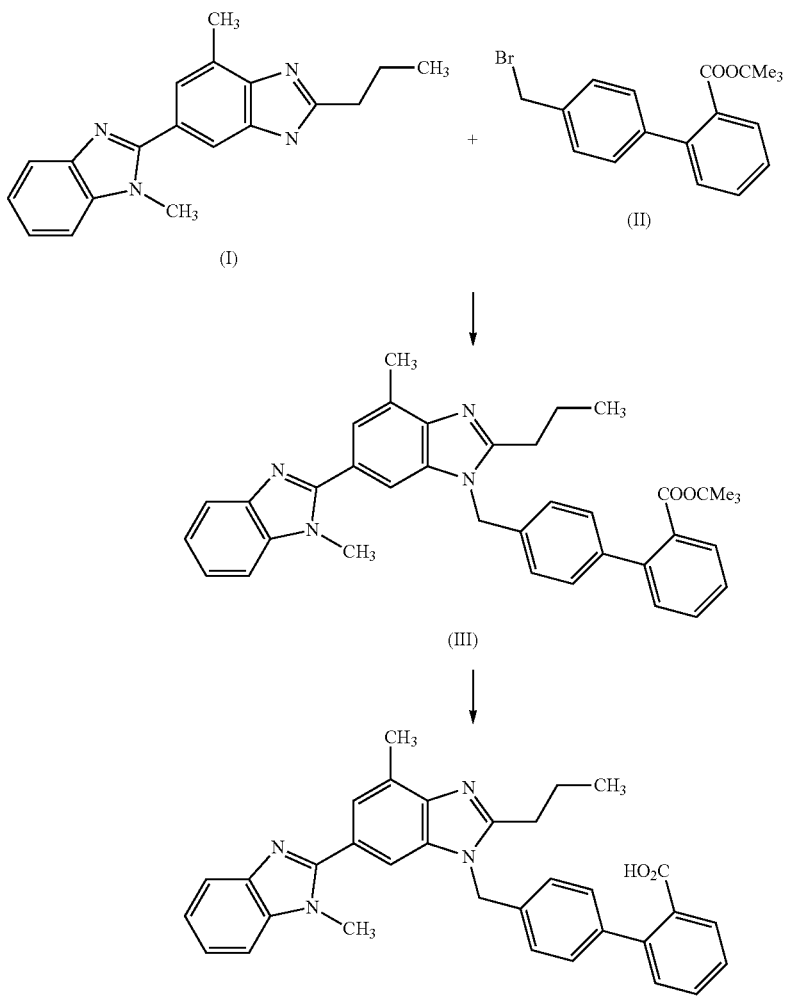

The coupling by nucleophilic substitution in the first reaction step is described in general terms in EP 502314 B1 as process b), while the saponification of the tert-butyl ester group on a laboratory scale using trifluoromethylacetic acid is described in the patent specification as Example 1. Industrially, saponification has up till now been carried out with concentrated aqueous hydrobromic acid. Scaling up the method of synthesis known from the patent specification to a large-scale industrial process was surprisingly beset with problems. Thus, the active substance prepared by the process known up till now can only be obtained in a satisfactory quality after running through a number of process steps (the crude product does not have the required purity until it has been recrystallized twice), while very long centrifuging and drying times are needed when isolating the substance. The telmisartan synthesized on an industrial scale according to Diagram 1 is obtained after working up in the form of a product which has to be subjected to a second crystallization step to complete the purification. In the crystallization step, which is absolutely essential, the morphology of the end product crystallizing out led to unforeseen problems.

The product precipitated in the form of long needles is difficult to filter, wash, and isolate and, because of the inclusion of solvent, is also characterized by a very long drying time and forms large, very hard lumps during the drying process. Grinding up these lumps results in a dry powder which has a strong tendency to electrostatic charging and is virtually impossible to pour.

The abovementioned undesirable properties of a product have always proved to be a major obstacle to the large-scale production of a compound as they stop the product being manufactured reproducibly in large quantities and allow a high degree of purity to be achieved only with considerable difficulty or at additional high technical costs.

The aim of the present invention is therefore to provide an alternative method of preparing telmisartan, which can be used on a large scale and allows telmisartan to be easily worked up, purified, and isolated without the disadvantages mentioned above.

BRIEF SUMMARY OF THE INVENTION

Surprisingly it has been found that from a technical point of view the reaction of 2-n-propyl-4-methyl-6-(1'-methylbenzimidazol-2'-yl)benzimidazole

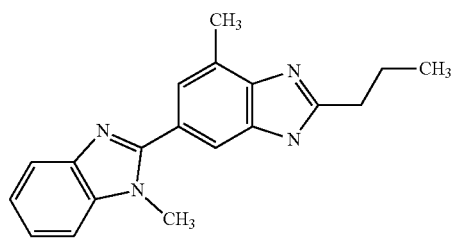

(I)

with a compound of general formula (IV)

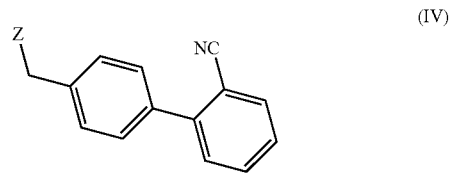

(IV)

wherein Z denotes a leaving group such as a halogen atom, for example, a chlorine, bromine, or iodine atom, or a substituted sulfonyloxy group, for example, a methanesulfonyloxy, phenylsulfonyloxy, or p-toluenesulfonyloxy group, to obtain the compound 2-cyano-4'-[2"-n-propyl-4"-methyl-6"-(1'"-methylbenzimidazol-2'"-yl)benzimidazol-1"-ylmethyl]biphenyl (V)

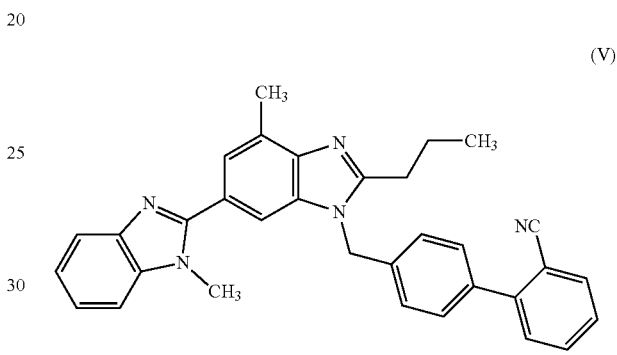

(V)

which may, if desired, be subjected to working up (Step (a)), and subsequent hydrolysis of the nitrile to the acid function (Step (b)) and, if desired, conversion of the compound (V) during working up into the hydrochloride, has considerable advantages over the synthesis shown in Diagram 1, and in particular does not have the drawbacks mentioned above for large-scale production by the conventional method.

DETAILED DESCRIPTION OF THE INVENTION

Step (a)

The reaction of the compound (I) with a compound of general formula (IV), wherein Z preferably denotes a halogen atom, particularly the bromine atom, is conveniently carried out in a solvent or mixture of solvents such as methylene chloride, diethyl ether, tetrahydrofuran, dioxane, dimethylsulfoxide, dimethylformamide, dimethylacetamide, dimethylformamide/tert-butanol, dimethylacetamide/tert-butanol, toluene, and benzene, optionally in the presence of an acid-binding agent such as sodium carbonate, potassium carbonate, sodium hydroxide, potassium hydroxide, sodium methoxide, potassium methoxide, potassium tert-pentoxide, potassium tert-butoxide, potassium n-butoxide, sodium hydride, triethylamine, or pyridine, while the latter two may also be used as solvents, for example, at a temperature between 0° C. and 100° C. The base is preferably used in powdered form if it is a solid.

Preferably, the reaction of the compound (I) with a compound of general formula (IV) is carried out in a solvent or mixture of solvents selected from dimethylsulfoxide, dimethylformamide, dimethylacetamide, dimethylformamide/tert-butanol, and dimethylacetamide/tert-butanol in the presence of sodium hydroxide, potassium hydroxide, or potassium tert-butoxide at a temperature between 0° C. and 30° C.

Particularly preferably, the reaction of the compound (I) with a compound of general formula (IV) is carried out in dimethylacetamide or dimethylacetamide/tert-butanol in the presence of potassium hydroxide at a temperature between 0° C. and 20° C.

Working Up

After the reaction has ended, the solvent is removed, for example, distilled off in a water-jet vacuum, and the residue is treated with a solvent in which the nitrile (V) has only limited solubility or is moderately soluble in the heat, for example, with an alcohol such as methanol, ethanol, n-propanol, isopropanol, n-butanol or isobutanol, with an aromatic hydrocarbon such as benzene or toluene, with an ethereal solvent such as diethyl ether, tetrahydrofuran, dioxane, or tert-butylmethylether, the ethereal solvents and particularly tert-butylmethylether being preferred, or with water. The crystals, which may be precipitated after cooling to 10° C. to 20° C., are suction filtered and washed first with the solvent used and then with water. If necessary, the product is dried at elevated temperature, for example at 50° C. to 100° C., in a vacuum drying cupboard. The nitrile (V) is generally obtained in excellent yields between 80% and 90% of theory and with excellent quality (purity according to HPLC >99.5%).

Step (b)

The subsequent hydrolysis of the nitrile function into a carboxy group is conveniently carried out in water, in an organic solvent, or in a mixture of an organic solvent with water, while the organic solvent may be, for example, methanol, ethanol, n-propanol, isopropanol, tetrahydrofuran, dioxane, ethylene glycol, propylene glycol, diglyme, dimethylsulfoxide, or diethylene glycol monomethyl ether, in the presence of an acid such as trifluoroacetic acid, trichloroacetic acid, hydrochloric acid, sulfuric acid, or phosphoric acid or in the presence of a base such as lithium hydroxide, sodium hydroxide, potassium hydroxide, cesium hydroxide, or calcium hydroxide or the anhydrides thereof; at temperatures between 80° C. and 200° C., while the water needed for the reaction may also be a constituent of one of the reagents used, e.g., one of the abovementioned aqueous acids, or may be generated under the reaction conditions from the reagents, possibly from one of the abovementioned alkali metal hydroxides.

Preferably, the hydrolysis of the nitrile function is carried out in a high-boiling solvent system selected from ethylene glycol/water and propylene glycol/water, in the presence of a base, potassium hydroxide being particularly suitable, at temperatures between 140° C. and 200° C., particularly at a temperature between 155° C. and 185° C.

Working Up

After the reaction has ended, the solvent is removed, for example, distilled off in a water-jet vacuum, the residue is diluted with water and taken up in hydrochloric acid, for example, with 5% to approximately 32% concentrated hydrochloric acid, preferably with 5% to 20% hydrochloric acid, whereupon telmisartan hydrochloride crystallizes out. The crystal suspension is cooled to 10° C. to 25° C. if necessary and may be stirred at this temperature for a certain length of time, for example up to 3 hours. After the crystals have been suction filtered, they are washed with water and if necessary dried in a vacuum drying cupboard at elevated temperature, for example, at 50° C. to 120° C.

Telmisartan in acid form can be liberated from the telmisartan hydrochloride in the usual way, e.g., by titration with aqueous alkali metal hydroxide solution. For example, the acid form is liberated analogously to the method described in WO 0043370 (page 3, line 6, to page 4, line 38, and Examples 1 to 3).

For large-scale production the process according to the invention has the following advantages inter alia deserving special mention:
  compounds of formula (IV), particularly 4'-bromomethyl-2-cyanobiphenyl, are mass produced and may be obtained cheaply;
  the coupling of components (I) and (IV) according to Step (a) may be carried out in a high concentration and at a correspondingly high throughput, while working up particularly using tert-butylmethylether yields the nitrile (V) as a precipitate which is easy to filter and wash, thus dispensing with the need for additional laborious working up procedures;
  the nitrile (V) is obtained in excellent yields of between 80% and 90% of theory and with excellent quality (purity according to HPLC >99.5%);
  the saponification of the nitrile (V) in Step (b) also produces excellent yields >95% of theory; and
  the end product telmisartan may be isolated either as an ampholyte or, preferably, by precipitation with hydrochloric acid as a hydrochloride which is easy to filter and hence easy to purify.

The following procedure is used, in a particularly preferred manner according to the invention:

Step (a):

All the quantities specified relate to a batch size of 0.1 mol of the compound (I) and if the batch size is altered must be multiplied by a corresponding factor.

50 mL to 200 mL, preferably 80 mL to 120 mL, of solvent per 0.1 mol of the compound (I) is placed in a suitably dimensioned reaction vessel, the compound (I) is suspended in the solvent and 0.1 mol to 0.2 mol of base, preferably 0.102 mol to 0.12 mol, are added batchwise thereto with stirring, while the temperature is maintained at between 10° C. and 50° C., preferably 15° C. to 30° C., and when the exothermic reaction has ended stirring may be continued for up to another 3 hours at this temperature. The mixture is cooled to approximately 0° C. to 10° C., for example, approximately 5° C., and then a mixture of 0.1 mol to 0.2 mol of a compound of general formula (IV), preferably 0.100 mol to 0.12 mol, with 50 mL to 200 mL solvent (per 0.1 mol of the compound (IV)) is added dropwise at 10° C. to 30° C., preferably at approximately 20° C. The reaction mixture is optionally maintained at approximately 0° C. to 20° C., preferably 5° C. to 10° C., by cooling with the ice bath. Then it may be rinsed out with a few mL of solvent and stirred for up to another 3 hours at 0° C. to 20° C.

In another embodiment the base is placed in 30 mL to 100 mL of solvent, preferably dimethylformamide, dimethylacetamide, dimethylformamide/tert-butanol, or dimethylacetamide/tert-butanol, at 10° C. to 30° C., stirred for up to an hour at about 20° C., for example, and then a suspension of the compound (I) in 30 mL to 100 mL solvent is slowly metered in at this temperature. All the other steps are the same as in the previous embodiment. The solvent mixtures specified are used in a ratio by volume of amide to tert-butanol is 10:1 to 2.5:1, for example, 5:1.

Working Up

The solvent is conveniently largely distilled off under reduced pressure, for example, under a water-jet vacuum, whereupon the product crystallizes out. After the residue has cooled to approximately 40° C. to 80° C., preferably about 60° C., it is diluted with 100 mL to 300 mL of solvent (per 0.1 mol batch size, based on compound (I)), preferably tert-butylmethylether, and stirred for up to 5 hours without any input of energy. The mixture is cooled to 0° C. to 30° C., preferably 15° C. to 20° C., and stirred for up to a further 5 hours at this temperature. The crystals are suction filtered and washed batchwise with 50 mL to 150 mL of the solvent and then with 200 mL to 300 mL of water. The product is dried in the vacuum drying cupboard at 50° C. to 100° C., preferably about 60° C.

Step (b):

Unless otherwise stated, all the amounts specified are based on a batch size of 0.05 mol of the compound (V) and must be multiplied by a corresponding factor if the batch size is altered.

0.05 mol of the compound (V), 200 mL to 300 mL of the organic solvent, 0.5 mL to 5 mL of water and 0.3 mol to 0.5 mol of the base are combined and heated to the boiling temperature of the solvent system used, i.e., if the preferred ethylene glycol/water mixture is used, it is heated to 140° C. to 200° C., preferably to 155° C. to 185° C. The mixture is stirred for up to 24 hours at this temperature.

In another embodiment, 0.361 mol of the nitrile (V) are placed in 1.5 L to 2 L of the organic solvent, preferably ethylene glycol, 25 mL to 50 mL of water and 2.5 mol to 3 mol of the base are added and the mixture is heated to 140° C. to 200° C., preferably to 155° C. to 185° C., for up to 24 hours, with stirring. All the other steps correspond to those in the previous embodiment.

Working Up

The amounts given are based on a batch size of 0.05 mol of compound (V). The solvent is conveniently eliminated under reduced pressure, for example distilled off under a water-jet vacuum, the residue is diluted with 30 mL to 100 mL of water, preferably about 5 mL, and stirred into a mixture of 100 mL to 150 mL of water (preferably about 125 mL) and 40 mL to 60 mL (preferably about 50 mL) of concentrated hydrochloric acid (approximately 32%), possibly rinsing with water. The telmisartan hydrochloride that crystallizes out is cooled to 10° C. to 25° C. and is stirred for up to 3 hours at this temperature. After the crystals have been suction filtered, they are washed with 50 mL to 200 mL of water and dried at 50° C. to 120° C. in a vacuum drying cupboard.

The Examples that follow serve to illustrate the invention and relate to exemplifying embodiments of the methods of synthesis according to the invention for preparing telmisartan, but without restricting the invention to their contents.

Example 1

2-cyano-4'-[2"-n-propyl-4"-methyl-6"-(1'''-methyl-benzimidazol-2'''-yl)benzimidazol-1"-ylmethyl]biphenyl 32.24 g of 2-n-propyl-4-methyl-6-(1'-methylbenzimidazol-2'-yl)benzimidazolexH$_2$O is placed in 100 mL of dimethylacetamide (DMA), and 11.8 g of potassium tert-butoxide is added batchwise with stirring at approximately 20° C. and then the mixture is stirred for one hour at about 20° C. The mixture is cooled to 5° C. and then a mixture of 28.6 g of 4-bromomethyl-2'-cyanobiphenyl and 95 mL of DMA (dissolved at approximately 20° C.) is added dropwise over about 30 minutes. The temperature of the reaction mixture is maintained at approximately 5° C.-10° C. by cooling with the ice bath. Then it is rinsed with 5 mL of DMA and stirred for a further 1.5 hours at 5° C. to 10° C.

The solvent is largely distilled off under a water-jet vacuum, during which time the product crystallizes out. The residue is cooled to 60° C., diluted with 230 mL of tert-butylmethylether and stirred for 1 hour without any energy input, then cooled to 15° C. to 20° C. and stirred for another hour at this temperature. The crystals are suction filtered, washed batchwise with 100 mL of tert-butylmethylether, then with 250 mL of water, and then dried in a vacuum drying cupboard at 80° C. Yield: 43.3 g (87.5% of theory); melting point: 196° C.-197° C.; HPLC: >99.9%.

Example 2

2-cyano-4'-[2"-n-propyl-4"-methyl-6"-(1'''-methyl-benzimidazol-2'''-yl)benzimidazol-1"-ylmethyl]biphenyl 32.24 g of 2-n-propyl-4-methyl-6-(1'-methylbenzimidazol-2'-yl)benzimidazolexH$_2$O is placed in 100 mL of DMA, and 6.9 g of potassium hydroxide (powder) is added batchwise with stirring at approximately 20° C. and then stirred for one hour at about 20° C. to 25° C. The mixture is cooled to 5° C. and then 28.6 g of 4-bromomethyl-2'-cyanobiphenyl in 95 mL of DMA (dissolved at approximately 20° C.) is added dropwise over approximately 30 minutes. The temperature of the reaction mixture is maintained at approximately 5° C. to 10° C. by cooling with the ice bath. Then it is rinsed with 5 mL of DMA and stirred for a further 1.5 hours at 5° C. to 10° C.

The solvent is largely distilled off under a water-jet vacuum, during which time the product crystallizes out. The residue is cooled to 60° C., diluted with 225 mL of tert-butylmethylether, and stirred for 1 hour without any energy input, then cooled to 15° C. to 20° C. and stirred for another hour at this temperature. The crystals are suction filtered, washed batchwise with 100 mL of tert-butylmethylether, then with 250 mL of water, and then dried in a vacuum drying cupboard at 80° C. Yield: 40.45 g (81.7% of theory); melting point: 196° C.-197° C.; HPLC: >99.9%.

Example 3

2-cyano-4'-[2"-n-propyl-4"-methyl-6"-(1'''-methyl-benzimidazol-2'''-yl)benzimidazol-1"-ylmethyl]biphenyl 6.9 g of potassium hydroxide (powder) is placed in 50 mL of DMA, stirred for 15 minutes at 20° C. to 25° C., and then a suspension of 32.24 of 2-n-propyl-4-methyl-6-(1'-methylbenzimidazol-2'-yl)benzimidazolexH$_2$O in 50 mL of DMA is metered in at 20° C. to 25° C. After it has all been added, the vessels are rinsed with 10 mL of DMA and then stirred for another hour at 20° C. to 25° C. The mixture is cooled to 5° C. and then 28.6 g of 4-bromomethyl-2'-cyanobiphenyl in 95 mL of DMA (dissolved at approximately 20° C.) is metered in. The temperature of the reaction mixture is maintained at approximately 5° C. to 10° C. by cooling with the ice bath. Then it is rinsed with 5 mL of DMA and stirred for a further hour at 5° C. to 10° C.

The solvent is largely distilled off under a water jet vacuum, during which time the product crystallizes out. The residue is cooled to 60° C., diluted with 250 mL of tert-butylmethylether, and stirred for 2 hours without any input of energy. The crystals are suction filtered, washed batchwise with 100 mL of tert-butylmethylether, then with 250 mL of water, and then dried in a vacuum drying cupboard at 80° C. Yield: 43.37 g (87.5% of theory); melting point: 196° C.-198° C.; HPLC: 99.1%.

Example 4

2-cyano-4'-[2''-n-propyl-4''-methyl-6''-(1'''-methyl-benzimidazol-2'''-yl)benzimidazol-1''-ylmethyl]biphenyl 53.4 g of potassium hydroxide (powder) is placed in 385 mL of DMA and then a suspension of 248.25 g of 2-n-propyl-4-methyl-6-(1'-methylbenzimidazol-2'-yl)benzimidazole×H₂O in 385 mL of DMA are metered in at 20° C. to 25° C. After it has all been added, the vessels are rinsed with 77 mL of DMA and then stirred for another hour at 20° C. to 25° C. The mixture is cooled to 5° C. and then 209.5 g of 4-bromomethyl-2'-cyanobiphenyl in 731.5 mL of DMA (dissolved at approximately 20° C.) is metered in. The temperature of the reaction mixture is maintained at approximately 5° C.-10° C. by cooling with the ice bath. Then it is rinsed with 38.5 mL of DMA and stirred for a further hour at 5° C.-10° C.

The solvent is largely distilled off under a water jet vacuum, during which time the product crystallizes out. The residue is cooled to 60° C., diluted with 1925 mL of tert-butylmethylether and stirred for 2 hours without any energy input. The crystals are suction filtered, washed batchwise with 770 mL of tert-butylmethylether/DMA (9:1), then with 1925 mL of water, and twice with 250 mL of tert-butylmethylether, and then dried at 80° C. in a vacuum drying cupboard. Yield: 322.15 g (84.4% of theory); melting point: 197° C.-198.5° C.; HPLC: 99.6%.

Example 5

Telmisartan×HCl 25 g of 2-cyano-4'-[2''-n-propyl-4''-methyl-6''-(1'''-methylbenzimidazol-2'''-yl)benzimidazol-1''-ylmethyl]biphenyl, 250 mL of ethylene glycol, 0.9 mL of water. and 24.75 g of caustic potash (>85%) are combined and heated to 160° C. with stirring. The mixture is stirred for 13.5 hours at this temperature.

The solvent is largely distilled off under a water-jet vacuum, the residue is cooled to 100° C., diluted with 50 mL of water, and stirred into a mixture of 125 mL of water and 50 mL of concentrated hydrochloric acid (approximately 32%), rinsing with 50 mL of water. The telmisartan hydrochloride that crystallizes out is cooled to 15° C. to 20° C. and stirred for approximately 1 hour at this temperature. After the crystals have been suction filtered, they are washed with 100 mL of water and dried in a vacuum drying cupboard at 100° C. Yield: 27.3 g (98.2% of theory); HPLC: 99.9%.

Example 6

Telmisartan×HCl 179 g of 2-cyano-4'-[2''-n-propyl-4''-methyl-6''-(1'''-methylbenzimidazol-2'''-yl)benzimidazol-1''-ylmethyl]biphenyl is placed in 1611 mL of ethylene glycol, 32.5 mL of water, and 178.7 g of potassium hydroxide (powder) are added and the mixture is heated to 150° C. to 160° C. with stirring. The mixture is stirred for approximately 15 hours at this temperature and then cooled to 100° C.

The solvent is largely distilled off under a water jet vacuum, the residue is cooled to 100° C., diluted with 358 mL of water, and stirred into a mixture of 716 mL of water and 358 mL of concentrated hydrochloric acid (approximately 32%), rinsing with 179 mL of water. The telmisartan hydrochloride that crystallizes out is stirred for one hour at 60° C., cooled to 15° C. to 20° C. and stirred for approximately 1 more hour at this temperature. After the crystals have been suction filtered, they are washed with 716 mL of water and dried in a vacuum drying cupboard at 100° C. Yield: 192.1 g (96.5% of theory); HPLC: >99.9%.

Example 7

Telmisartan 5.51 g of telmisartan×HCl is dissolved in 50 mL of 40% acetic acid while refluxing. Then the brown solution is filtered hot through 1.1 g of charcoal, washed with 2.5 mL of 40% acetic acid, and 2.5 mL of 4N NaOH is added dropwise to the light brown filtrate with stirring at 80° C. to 90° C. The telmisartan crystallizes out, the suspension is diluted with 30 mL of water and slowly cooled to ambient temperature. The telmisartan is suction filtered and washed with 50 mL of water. The telmisartan is dried at 80° C. in a vacuum drying cupboard. Yield: 4.80 g (93.3% of theory).

We claim:
1. A process for preparing telmisartan, comprising:
   (a) reacting 2-n-propyl-4-methyl-6-(1'-methylbenzimidazol-2'-yl)benzimidazole (I):

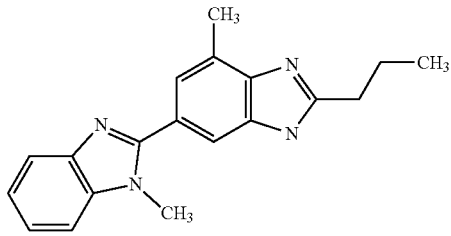 [SMILES: CCCc1nc2c(C)cc(-c3nc4ccccc4n3C)cc2[nH]1]

with a compound of formula (IV):

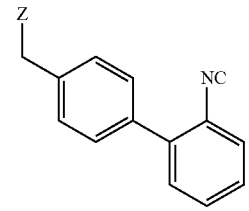

wherein Z is a leaving group, in a first solvent selected from methylene chloride, diethyl ether, tetrahydrofuran, dioxane, dimethylsulfoxide, dimethylformamide, dimethylacetamide, dimethylformamide/tert-butanol, dimethylacetamide/tert-butanol, toluene, benzene or a mixture thereof, to obtain a compound 2-cyano-4'-[2''-n-propyl-4''-methyl-6''-(1'''-methylbenzimidazol-2'''-yl)-benzimidazol-1''-ylmethyl]biphenyl (V):

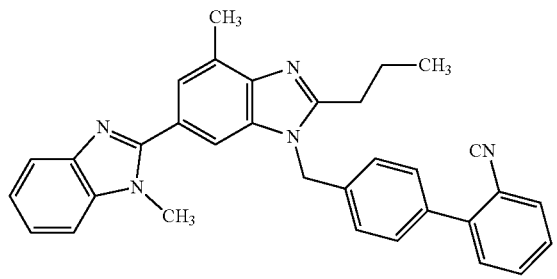

and (b) hydrolyzing the nitrile function of compound (V) obtained from step (a) into the acid function in a second solvent selected from water, methanol, ethanol, n-propanol, isopropanol, tetrahydrofuran, dioxane, ethylene glycol, propyleneglycol, diglyme, dimethylsulfoxide, diethylene glycol monomethyl ether or a mixture thereof, in the presence of a base and at a temperature between 80° C. and 200° C., to obtain telmisartan.

2. The process according to claim 1, wherein the product of step (a) is worked up before step (b) is performed.

3. The process according to claim 1, wherein the telmisartan product of step (b) is worked up and converted into the hydrochloride.

4. The process according to claim 1, wherein the product of step (a) is worked up before step (b) is performed and the telmisartan product of step (b) is worked up and converted into the hydrochloride.

5. The process according to claim 1, wherein Z is a halogen atom or a substituted sulfonyloxy group.

6. The process according to claim 1, wherein Z is a bromine atom.

7. The process according to claim 1, wherein step (a) is carried out in the presence of an acid-binding agent.

8. The process according to claim 7, wherein the acid-binding agent is selected from sodium carbonate, potassium carbonate, sodium hydroxide, potassium hydroxide, sodium methoxide, potassium methoxide, potassium tert-pentoxide, potassium tert-butoxide, potassium n-butoxide, sodium hydride, triethylamine, and pyridine.

9. The process according to claim 1, wherein step (a) is carried out at a temperature between 0° C. and 100° C.

10. The process according to claim 2, wherein step (a) is carried out at a temperature between 0° C. and 100° C.

11. The process according to claim 3, wherein step (a) is carried out at a temperature between 0° C. and 100° C.

12. The process according to claim 4, wherein step (a) is carried out at a temperature between 0° C. and 100° C.

13. The process according to claim 1, wherein in step (a) the reaction of the compound (I) with the compound of formula (IV) is carried out in a first solvent selected from dimethylsulfoxide, dimethylformamide, dimethylacetamide, dimethylformamide/tert-butanol, and dimethylacetamide/tert-butanol in the presence of sodium hydroxide, potassium hydroxide, or potassium tert-butoxide at a temperature between 0° C. and 30° C.

14. The process according to claim 1, wherein after step (a) has been carried out, the first solvent is removed and the residue is treated with a supplementary solvent in which the compound (V) has only limited solubility or is moderately soluble in the heat.

15. The process according to claim 14, wherein crystals of the compound (V) are precipitated by cooling the supplementary solvent containing the compound (V).

16. The process according to claim 15, wherein the crystals of the compound (V) are suction filtered.

17. The process according to claim 15, wherein the crystals of the compound (V) are suction filtered and washed with the supplementary solvent.

18. The process according to claim 16, wherein the crystals of the compound (V) are dried at elevated temperature.

19. The process according to claim 14, wherein the supplementary solvent is an alcohol, an aromatic hydrocarbon, an ether, or water.

20. The process according to claim 1, wherein the second solvent is methanol, ethanol, n-propanol, isopropanol, tetrahydrofuran, dioxane, ethylene glycol, propyleneglycol, diglyme, dimethylsulfoxide, or diethylene glycol monomethyl ether.

21. The process according to claim 1, wherein the base is selected from lithium hydroxide, sodium hydroxide, potassium hydroxide, cesium hydroxide, calcium hydroxide or an anhydride thereof.

22. The process according to claim 1, wherein the second solvent is a high-boiling solvent system selected from ethylene glycol/water and propyleneglycol/water and step b) is conducted at temperatures at a temperature between 140° C. and 200° C.

23. The process according to claim 22, wherein the base is potassium hydroxide and the temperature is between 155° C. and 185° C.

24. The process according to claim 1, wherein the telmisartan product of step (b) is worked up by eliminating the second solvent, the residue obtained is optionally diluted with water and taken up in aqueous hydrochloric acid, and the telmisartan hydrochloride that crystallizes out is cooled if necessary, then suction filtered and optionally dried.

25. The process according to claim 24, wherein the telmisartan hydrochloride is converted into the acid form.

26. The process according to claim 1, wherein the base for step b) is selected from lithium hydroxide, sodium hydroxide, potassium hydroxide, cesium hydroxide, calcium hydroxide or an anhydride thereof and step b) is conducted at a temperature between 140° C. and 200° C.

* * * * *